United States Patent [19]

Takaya et al.

[11] 4,246,405
[45] Jan. 20, 1981

[54] METHOD FOR PREPARATION OF β-LACTAM COMPOUND

[75] Inventors: Takao Takaya, Kawanishi; Hiromu Kochi, Sakai; Takashi Masugi, Kitamachi, all of Japan

[73] Assignee: Fujisawa Pharmaceutical Company, Limited, Osaka, Japan

[21] Appl. No.: 911,540

[22] Filed: Jun. 1, 1978

[30] Foreign Application Priority Data

Jun. 3, 1977 [JP] Japan .................... 52-65990

[51] Int. Cl.³ .......................... C07D 501/02
[52] U.S. Cl. ...................... 544/16; 544/27; 544/22
[58] Field of Search .............. 544/28, 16, 27, 22, 544/30

[56] References Cited

U.S. PATENT DOCUMENTS

| | | | |
|---|---|---|---|
| 4,013,651 | 3/1977 | Spitzer | 544/16 |
| 4,065,618 | 12/1977 | Spitzer | 544/16 |
| 4,065,621 | 12/1977 | Spitzer | 544/16 |
| 4,081,595 | 3/1978 | Nagata et al. | 544/16 |

Primary Examiner—Nicholas S. Rizzo
Attorney, Agent, or Firm—Oblon, Fisher, Spivak, McClelland & Maier

[57] ABSTRACT

A process for preparing a 7-substituted-3-cephem-4-carboxylic acid of the formula:

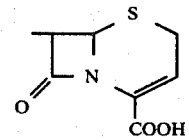

or a pharmaceutically acceptable salt thereof, which comprises
subjecting a corresponding 7-substituted-3-organic sulfonyloxy-3-cephem-4-carboxylic acid ester of the formula

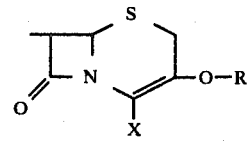

wherein R is a residue of an organic sulfonic acid, X is esterified carboxy which is an alkoxylcarbonyl, haloalkoxycarbonyl, substituted or unsubstituted aralkoxycarbonyl, benzhydryloxycarbonyl or trityloxycarbonyl, or a pharmaceutically acceptable salt thereof,
to hydrogenolysis using a combination of a metal and formic acid as a reducing reagent.

11 Claims, No Drawings

METHOD FOR PREPARATION OF β-LACTAM COMPOUND

This invention relates to a new method for preparation of β-lactam compound, especially 7-substituted-3-cephem-4-carboxylic acid, which is a useful antimicrobial agent or an intermediate for preparing the same.

More particularly, this invention relates to a method for the preparation of 7-substituted-3-cephem-4-carboxylic acid from 7-substituted-3-organic sulfonyloxy-3-cephem-4-carboxylic acid ester by a hydrogenolysis using a metal and formic acid.

In the cephalosporin chemistry, there are already known the prior arts disclosing the methods for preparation of 7-substituted-3-cephem-4-carboxylic acid from 7-substituted-3-hydroxy(or chloro)-3-cephem-4-carboxylic acid ester as illustrated in the following scheme:

(1) Japanese Published Unexamined Patent Application Laid Open No. 49-49989:

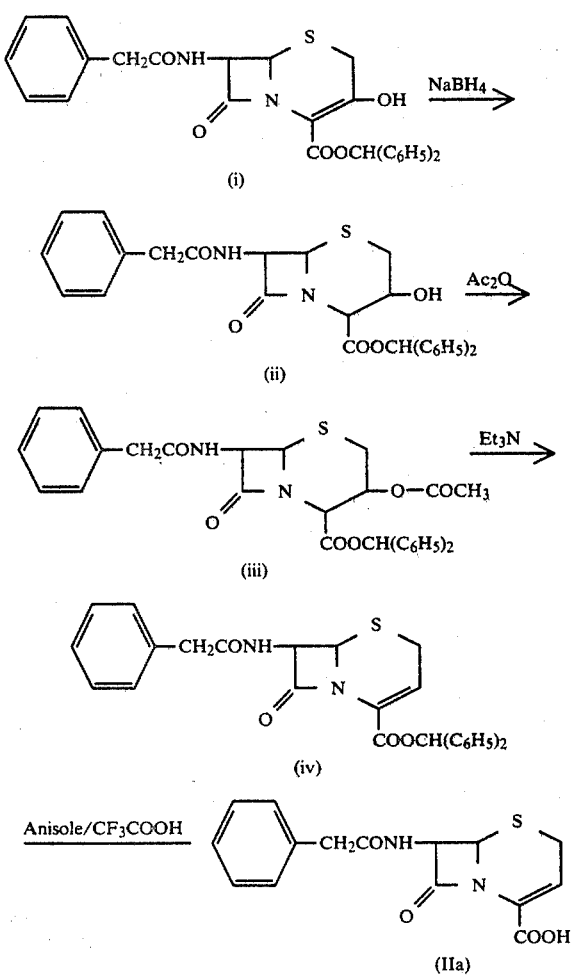

(2) Japanese Published Unexamined Patent Application Laid Open No. 52-59186:

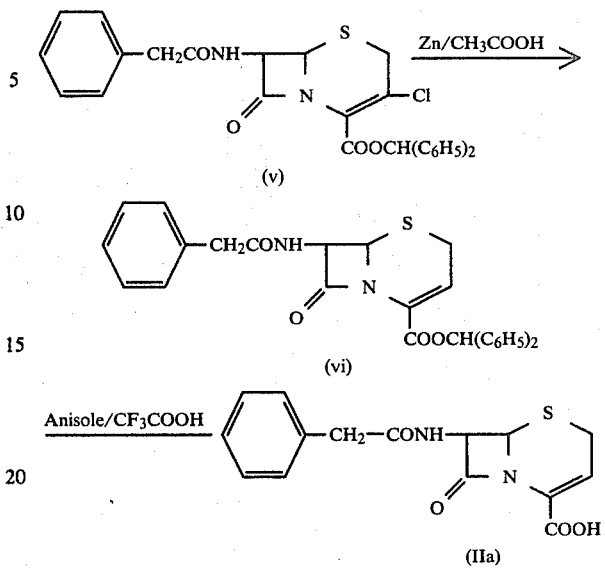

It is to be noted, that, in the latter method (2), the starting compound (v) is known to be prepared from the corresponding 3-hydroxy-3-cephem compound (i) by chlorination.

Further, the starting compound (i) is known to be synthesized from a penicillin compound, e.g. an ester of penicillin G, or from a cephalosporin compound, e.g. 7-phenylacetamidocephalosporanate, via a number of chemical reaction steps, but it was one problem that nonprotected free carboxylic acid form per se of the compound (i) is too unstable to be handled because it tends to be so easily decomposed (e.g. decarboxylation) due to its β-keto-carboxylic acid or its tautomeric β-enol-carboxylic acid structure in its molecule. Accordingly, the 7-substituted 3-hydroxy-3-cephem-4-carboxylic acid was to be protected at least on its carboxy function such as the ester (i) in the synthesis processes as illustrated above and thereafter the protected carboxy function of the 3-cephem compound (iv) is to be transformed into the free carboxy group.

The present inventors have been studying for providing an economical manufacturing processes of 7-substituted-3-cephem-4-carboxylic acid, and found out a new method of the preparation of the same from 7-substituted-3-organic sulfonyloxy-3-cephem-4-carboxylic acid ester by using a metal and specified formic acid as a reagent. That is, the present inventors found out that the use of the specified formic acid as reagent in the reaction can provide directly 7-substituted-3-cephem-4-carboxylic acid from 7-substituted-3-organic sulfonyloxy-3-cephem-4-carboxylate, while almost none of 7-substituted-3-cephem-4-carboxylate and/or 7-substituted-3-organic sulfonyloxy-3-cephem-4-carboxylic acid can be detected in the reaction mixture.

Accordingly, it is to be noted that the process of the present invention is characterized in providing 7-substituted-3-cephem-4-carboxylic acid by eliminating both of the organic sulfonyloxy group and the ester moiety of the starting 7-substituted-3-organic sulfonyloxy-3-cephem-4-carboxylate almost simultaneously at once.

The above new finding is entirely unexpected and surprising one, and so have never been able to be anticipated by the skilled in the cephalosporin chemistry even from the prior arts as mentioned above.

The method of the present invention comprises subjecting a 7-substituted-3-organic sulfonyloxy-3-cephem-4-carboxylic acid ester of the formula:

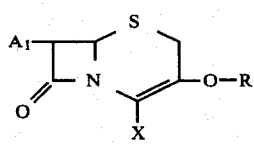   (I)

wherein R is a residue of organic sulfonic acid, and X is esterified carboxy, or its salt to reduction with a metal and formic acid to provide a 7-substituted-3-cephem-4-carboxylic acid of the formula:

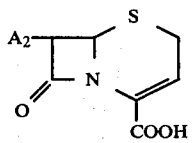   (II)

or a salt thereof. $A_1$ and $A_2$ represent the substituent in the 7-position of the respective compounds.

The starting compound (I) can be prepared from the corresponding 3-hydroxy-3-cephem-4-carboxylic acid ester of the formula:

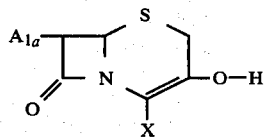   (Ia)

wherein X is as defined above and $A_{1a}$ represents a substituent in the 7-position, by reacting with an organic sulfonic acid of the formula:

   (III)

R—OH wherein R is as defined above, in a conventional manner which is well known in the art.

The industrial value of this novel one-step synthesis method will be clearly understood in the following points as compared with the prior methods. (a) This process can shorten the sequence of unit processes by one unit as compared with those of the prior method (2) and by two unit as compared with those of the prior method (1) for the preparation of the 7-substituted-3-cephem-4-carboxylic acid (II) from the corresponding 3-hydroxy(or chloro)-3-cephem-4-carboxylic acid ester (V) or (i) respectively. (b) This process can be always conducted by simplified procedure as illustrated in detail hereafter.

In the 7-substituted-3-organic sulfonyloxy-3-cephem-4-carboxylic acid ester of the formula (I), the substituent at the 7th position thereof may include substituent such as amino, acylamino and protected amino.

The "acylamino" means an amino bearing always an acyl group which is conventionally adopted in the penicillin, cephalosporin and their analogue and homologue chemistry field as illustrated as follows:

Alkanoyl such as formyl, acetyl, propionyl, butyryl, isobutyryl, valeryl, pivaloyl, hexanoyl, lauroyl, palmitoyl, stearoyl and the like;

cycloalkanecarbonyl such as cyclopropanecarbonyl, cyclobutanecarbonyl, cyclopentanecarbonyl, cyclohexanecarbonyl, and the like;

alkenoyl such as acrylpyl, crotonyl, 2-methylacryloyl, and the like;

aroyl such as benzoyl, toluoyl, xyloyl, naphthoyl, 4-isopropylbenzoyl and the like;

alkoxycarbonyl such as methoxycarbonyl, ethoxycarbonyl isopropoxycarbonyl, isobutoxycarbonyl, 1,1-dimethylpropoxycarbonyl, tert-butoxycarbonyl, pentyloxycarbonyl, adamantyloxycarbonyl and the like;

aryloxycarbonyl such as phenoxycarbonyl, tolyloxycarbonyl, xylyloxycarbonyl and the like;

an alkanesulfonyl such as mesyl, ethanesulfonyl, and the like; arenesulfonyl such as benzenesulfonyl, tosyl and the like; saturated or unsaturated, monocyclic or polycyclic heterocyclicoxycarbonyl containing at least one, preferably up to five, hetero atom(s) such as oxygen, sulfur and nitrogen (e.g. 8-quinolyloxycarbonyl, pyridyloxycarbonyl, etc.);

saturated or unsaturated, monocyclic or polycyclic heterocycle-carbonyl containing at least one, preferably up to five, hetero atom(s) such as oxygen, sulfur and nitrogen (e.g. thenoyl, furoyl, nicotinoyl, isonicotinoyl, etc.);

arylcarbamoyl such as phenylcarbamoyl, tolylcarbamoyl and the like;

alkylcarbamoyl such as methylcarbamoyl, ethylcarbamoyl, dimethylcarbamoyl and the like;

an alkylthiocarbamoyl such as methylthiocarbamoyl, ethylthiocarbamoyl, dimethylthiocarbamoyl and the like;

arylthiocarbamoyl such as phenylthiocarbamoyl, tritylthiocarbamoyl and the like;

acyl derived from dibasic carboxylic acid such as succinyl, fumaroyl, phthaloyl and the like.

The above-mentioned acyl group may optionally have one or more, same or different substituent(s) at the optional position.

Suitable examples of such a substituent may include
aryl such as phenyl, tolyl, xylyl and the like; aroyl as mentioned above;
halogen such as chlorine, fluorine, bromine, and the like;
cyano; cycloalkyl such as cyclopropyl, cyclobutyl, cyclopentyl, cyclohexyl and the like;
alkoxy such as methoxy, ethoxy, propoxy, butoxy, pentyloxy, hexyloxy and the like;
alkylthio such as methylthio, ethylthio, propylthio, isopropylthio, butylthio, pentylthio, hexylthio and the like;
alkoxycarbonyl as mentioned above;
amino; hydroxy; hydroxyimino; alkoxyimino;
alkanoyloxy such as acetoxy, propionyloxy and the like;
aryloxy such as phenoxy, tolyloxy, xylyloxy and the like;
arylthio such as phenylthio, tolylthio, xylylthio and the like;
heterocyclic group such as thienyl, thiadiazolyl, thiazolyl, tetrazolyl, pyridyl, oxadiazolyl, benzothiazolon-3-yl and the like;
heterocyclic-thio or heterocyclic-oxy such as pyridyloxy, pyridylthio, thiadiazolylthio and the like;
alkyl such as methyl, ethyl, propyl, isopropyl, butyl, pentyl, hexyl and the like;
nitro; phenylazo; alkanesulfonyl such as mesyl, ethanesulfonyl, and the like;

alkanesulfonamido such as methanesulfonamido, ethanesulfonamido and the like;

alkanoylamino such as acetamido, propionamido and the like.

The above substituents, aryl, aryloxy, arylthio and heterocyclic group may optionally have further one or more substituent(s) such as alkoxy, halogen, alkyl, amino, alkanoylamino, nitro and the like.

The suitable examples of the acyl group having substituent(s) as mentioned above may include aroylalkanoyl such as phenylglyoxyloyl and the like;

haloalkanoyl such as chloroacetyl, dichloroacetyl, difluoroacetyl, trifluoroacetyl, chloropropionyl, chlorobutyryl, chlorovaleryl, trichloroacetyl, bromohexanoyl and the like; cyanoalkanoyl such as cyanoacetyl, cyanopropionyl and the like;

cycloalkylalkanoyl such as cyclopropylacetyl, cyclohexylacetyl and the like;

alkoxyalkanoyl such as methoxyacetyl, ethoxyacetyl, and the like;

alkylthioalkanoyl such as methylthioacetyl, ethylthiopropionyl, isopropylthioacetyl and the like;

alkoxycarbonylalkanoyl such as methoxycarbonylpropionyl, ethoxycarbonylacetyl, propoxycarbonylbutyryl and the like;

aralkanoyl such as phenylacetyl, tolylacetyl, phenylpropionyl and the like;

ar-alkanoyl substituted with amino such as phenylglycyl, phenylalanyl and the like;

aralkanoyl substituted with hydroxy such as mandelyl and the like;

alkanoyl substituted with aryl and alkanoyloxy such as 2-acetoxy-2-phenylacetyl and the like;

aryloxyalkanoyl which may be substituted with alkoxy, nitro or halogen, such as phenoxyacetyl, 3-methoxyphenoxyacetyl, 2-nitrophenoxyacetyl, 4-chlorophenoxyacetyl, 4-bromophenoxypropionyl, 2,5-dichlorophenoxyacetyl, 2-nitro-4-chlorophenoxyacetyl and the like;

arylthioalkanoyl which may be substituted with nitro or halogen, such as phenylthioacetyl, 2-nitrophenylthioacetyl, 4-chlorophenylthioacetyl and the like;

heterocyclicalkanoyl such as thienylacetyl, thiadiazolylacetyl, thiazolylacetyl, tetrazolylacetyl, pyridylacetyl, thienylpropionyl, benzothiazolon-3-ylacetyl, oxadiazolylacetyl and the like;

heterocyclic-alkanoyl substituted with alkyl or amino, such as methylthiazolylacetyl, aminothiazolylacetyl and the like;

heterocyclic-oxyalkanoyl such as pyridyloxyacetyl and the like;

heterocyclic-thioalkanoyl such as pyridylthioacetyl, thiadiazolylthioacetyl and the like;

aralkenoyl such as cinnamoyl and the like;

aroyl substituted with nitro, halogen, alkanesulfonyl, hydroxy, alkenesulfonamido, alkanoylamino, alkoxy, alkoxycarbonyl or cyano, such as 4-nitrobenzoyl, 4-chlorobenzoyl, 3-bromobenzoyl, 4-mesylbenzoyl, salicyloyl, 4-hydroxybenzoyl, 2-hydroxy-5-chlorobenzoyl, 4-methanesulfonamidophenyl, 4-acetamidobenzo, p-anisoyl, 4-propoxybenzoyl, 4-methoxycarbonylbenzoyl, 4-ethoxycarbonylbenzoyl, 4-cyanobenzoyl, 3,4,5-trimethoxybenzoyl and the like;

haloalkoxycarbonyl such as trichloroethoxycarbonyl, tribromoethoxycarbonyl and the like;

heterocyclic-alkoxycarbonyl such as 2-pyridylmethoxycarbonyl and the like;

cycloalkylalkoxycarbonyl such as 1-cyclopropylethoxycarbonyl and the like;

aralkoxycarbonyl which may be substituted with halogen, nitro, alkoxy or phenylazo, such as benzyloxycarbonyl, phenethyloxycarbonyl, diphenylmethoxycarbonyl, 2-bromobenzyloxycarbonyl, 4-nitrobenzyloxycarbonyl, 4-chlorobenzyloxycarbonyl, 4-bromobenzyloxycarbonyl, 3,4-dimethylbenzyloxycarbonyl, 4-(phenylazo)benzyloxycarbonyl, 4-methoxybenzyloxycarbonyl and the like;

haloaryloxycarbonyl such as 4-chlorophenoxycarbonyl and the like;

haloalkylcarbamoyl such as chloroethylcarbamoyl and the like.

The protected amino is intended to mean an amino which is protected by a conventional amino protective group which includes an easily removable acyl group; aralkyl such as benzyl, benzhydryl, trityl and the like; silyl group such as trialkylsilyl (e.g. trimethylsilyl, triethylsilyl), trialkoxysilyl (e.g. trimethoxysilyl), alkyldialkoxysilyl (e.g. methyldimethoxysilyl) and the like; organic stanyl group, and the like.

Suitable example of the "residue of an organic sulfonic acid" for R includes alkanesulfonyl such as mesyl, ethanesulfonyl, propanesulfonyl, butanesulfonyl, pentanesulfonyl, hexanesulfonyl and the like; arenesulfonyl such as benzenesulfonyl, toluenesulfonyl and the like. These residue may optionally have substituent(s) such as halogen (e.g. fluorine, chlorine, bromine, etc.); nitro and the like, among which preferred one is arenesulfonyl and more preferred one is benzenesulfonyl and tosyl.

The "esterified carboxy" for X includes an alkoxycarbonyl, preferably a branched alkoxycarbonyl (e.g. tert-butoxycarbonyl, neopentyloxycarbonyl, etc.), a haloalkoxycarbonyl, preferably halo(lower)alkoxycarbonyl (e.g. trichloromethoxycarbonyl, 2-iodoethoxycarbonyl, 2,2,2-trichloroethoxycarbonyl, etc.); a substituted or unsubstituted aralkoxycarbonyl, preferably substituted or unsubstituted benzyloxycarbonyl (e.g. benzyloxycarbonyl, 4-nitrobenzyloxycarbonyl, 4-methoxybenzyloxycarbonyl, 3,4-dimethoxybenzyloxycarbonyl, 4-hydroxy-3,5-di(tert)-butylbenzyloxycarbonyl etc.) benzhydryloxycarbonyl, trityloxycarbonyl, and the like, among which most preferred one is 2,2,2-trichloroethoxycarbonyl, and 4-nitrobenzyloxycarbonyl.

Suitable salt of the compound (I) and (II) includes an inorganic acid salt (e.g. hydrochloride, hydrobromide, sulfate, etc.); an organic acid salt (e.g. acetate, tartrate, etc.); an amino acid salt (e.g. arginine salt, histidine salt, etc.), and the like; a salt with an inorganic base such as alkali metal salt (e.g. sodium salt, potassium salt, etc.); a salt with an organic base such as trimethylamine salt, triethylamine salt, dicyclohexylamine salt, pyridinium salt and the like.

The reaction of this process is conducted by subjecting the compound (I) to reduction with an metal and formic acid.

Suitable metal used as a reagent in this process includes zinc, tin, iron and the like preferably zinc.

The reaction can be conducted in a solvent such as water, methanol, ethanol, tetrahydrofuran, N,N-dimethylformamide or any other solvent which does not adversely influence on the reaction, and a mixture thereof.

Formic acid used in this process as a reagent can be used in large excess amount as a solvent.

The reaction can be conducted within a range of cooling to heating, but preferably cooling to room temperature.

The substituent at the 7th position of the starting compound (I) may be occasionally modified and transformed into another different substituent in the course of the reaction and/or post-treatment, by suffering from side reaction (e.g. reduction, etc.), in case of the substituent bearing functional group(s) (e.g. nitro, the aforementioned silylamido, etc.) which is sensitive to the reaction condition of this process (e.g. reagent, solvent, temperature, etc.) and/or the post-treatment condition (e.g. neutralization, distillation, etc.). Such cases are also included within the scope of this synthesis process. And such sensitive functional group(s) of the starting compound (I) can be preferably protected, if desired, in advance of the reaction.

The object compound (II) in this invention can be isolated and purified by a conventional method adopted in the field of β-lactam chemistry (e.g. penicillin, cephalosporin and their hamologue and analogue). In this respect, it is to be noted that, in the step of isolating the object compound (II), formic acid used as a reagent can be easily removed off from the reaction mixture by simple distillation under milder condition such as slightly reduced pressure, lower temperature, etc. Such milder step of isolation can be said to be derived from the use of formic acid in this process, and can prevent the produced object compound (II) from its undesired decomposition and this point also constitutes a characteristic feature of this process.

The method of this invention is explained in detail by the following examples.

EXAMPLE 1

Zinc powder (4.0 g.) was added portionwise to a stirred solution of 2,2,2-trichloroethyl 7-(2-phenylacetamido)-3-tosyloxy-3-cephem-4-carboxylate (0.8 g.) in formic acid (16 ml.) over 3 minutes under ice-cooling. The mixture was stirred at the same temperature for 5 minutes and then filtered. The remaining zinc powder was washed with ethyl acetate. The filtrate and washings were combined together, washed three times with a saturated aqueous solution of sodium chloride, dried over magnesium sulfate and then evaporated to dryness in vacuo. The residue was pulverized by trituration with diisopropyl ether and the precipitates were collected by filtration to give 7-(2-phenylacetamido)-3-cephem-4-carboxylic acid (0.32 g.), Yield 78.1%.

I.R.$\nu_{max}^{Nujol}$: 3326, 1768, 1690, 1626, 1520, 1460 cm$^{-1}$

N.M.R. δ(DMSO-d$_6$, ppm): 3.55 (2H, s), 3.60 (2H, broad s), 5.03 (1H, d, J=5 Hz), 5.72 (1H, dd, J=9 Hz, 5 Hz), 6.49 (1H, broad t, J=5 Hz), 7.29 (5H, s), 9.12 (1H, d, J=9 Hz).

EXAMPLE 2

4-Nitrophenyl 7-amino-3-tosyloxy-3-cephem-4-carboxylate hydrochloride was treated in a similar manner to that of Example 3 to give 7-amino-3-cephem-4-carboxylic acid. mp>270° C.

I.R. $\nu_{max}^{Nujol}$: 3200, 1850, 1616, 1530, 1463 cm$^{-1}$.

N.M.R. δ(NaHCO$_3$+D$_2$O, ppm): 3.53 (1H, d, J=5 Hz), 3.59 (1H, d, J=3 Hz), 4.63 (1H, d, J=5 Hz), 5.06 (1H, d, J=5 Hz), 6.41 (1H, dd, J=5 Hz, 3 Hz).

EXAMPLE 3

Zinc powder (2.0 g.) was added portionwise to a stirred solution of 4-nitrobenzyl 7-(2-phenylacetamido)-3-tosyloxy-3-cephem-4-carboxylate (2.0 g.) in 90% formic acid (40 ml.) over 6 minutes under ice-cooling. The mixture was stirred at room temperature for an hour and then filtered. The remaining insoluble substances were washed with ethyl acetate. The filtrate and the washings were combined together and evaporated in vacuo. The residue was dissolved in ethyl acetate, washed with water, diluted hydrochloric acid and water in turn, dried over magnesium sulfate and then evaporated to dryness in vacuo. The oily residue was pulverized by trituration with diisopropyl ether and the solidified precipitates were collected by filtration to give 7-(2-phenylacetamido)-3-cephem-4-carboxylic acid (0.73 g.), Yield 71.5%.

What we claim is:

1. A process for preparing a 7-substituted-3-cephem-4-carboxylic acid of the formula:

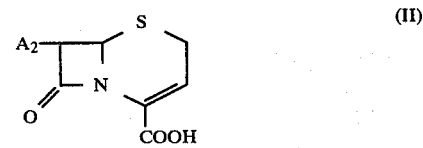

or pharmaceutically acceptable salt thereof, which comprises:
subjecting a solution of a corresponding 7-substituted-3-organic sulfonyloxy-3-cephem-4-carboxylic acid ester of the formula:

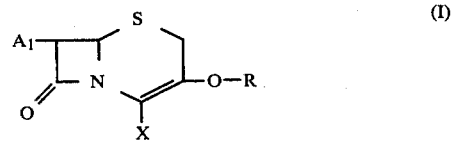

wherein R is an organic sulfonyl moiety which is a residue of an organic sulfonic acid which is unsubstituted or halo or nitro substituted alkanesulfonyl or arenesulfonyl, X is an esterified carboxy which is convertible to carboxy by hydrogenolysis and is alkoxylcarbonyl, haloalkoxycarbonyl, aralkoxycarbonyl, benzhydryloxycarbonyl, trityloxycarbonyl, 4-nitrobenzyloxycarbonyl, 4-methoxybenzyloxycarbonyl, 3,4-dimethoxybenzyloxycarbonyl, 4-hydroxy-3,5-di(tert)butylbenzyloxycarbonyl, or a pharmaceutically acceptable salt of compound I, to hydrogenolysis of the -OR moiety and of the esterified carboxy X by means of a reducing reagent which is iron, zinc or tin in admixture with formic acid, wherein each of A$_1$ and A$_2$ is a substituent in the 7-cephem position selected from the group consisting of amine, an acylamino, or a protected amino in which the protecting group is an easily removable protecting group other than an acyl group, and wherein the acyl moiety of said acylamino is selected from alkanoyl, cycloalkanecarbonyl, alkenoyl, aroyl, alkoxycarbonyl, adamaotyloxycarbonyl, aryloxycarbonyl, alkanesulfonyl, arenesulfonyl, 8-quinolyloxycarbonyl, pyridyloxycarbonyl, thenoyl, furoyl, nicotinoyl, isonicotinoyl, arylcarbamoyl, alkylcarbamoyl, alkylthiocarbamoyl, phenylthiocarbamoyl, tritylthiocarbamoyl, succinyl, fumaroyl, phthaloyl, aroylalkanoyl, haloalkanoyl, cyanoalkanoyl, cycloalkylalkanoyl, alkoxyalkanoyl, alkylthioalkanoyl, alkoxycarbonylalkanoyl, aralkanoyl, ar-(amino)alkanoyl, ar(hydroxy)alkanoyl, aryl(alkanoyloxy)alkanoyl, aryloxyalkanoyl, ((alkoxy, nitro, or halo)aryloxy)alkanoyl, 2-nitro-4-chlorophenoxyacetyl, arylthioalkanoyl, nitroarylthioalkanoyl, chloroarylthioalkanoyl, thienylacetyl, thiadiazolylacetyl, thiazolylacetyl, tetrazolylacetyl, pyridylacetyl, thienylpropionyl, benzothiazolon-3-ylacetyl, oxadiazolyacetyl, methylthaizolylacetyl, aminothazolylacetyl, pyridyloxyacetyl, pyridylthioacetyl, thiadiazolylthioacetyl, aralkenoyl, (nitro,halo, alkanesulfonyl, hydroxy, alkanesulfonamido, alkanoylamino, alkoxy, alkoxycarbonyl or cyano) aroyl, 2-hydroxy-5-chlorobenzoyl, haloalkoxycarbonyl, 2-pyridylmehtoxycarbonyl, cycloalkyloxycarbonyl, aralkoxycarbonyl, (halo, nitro, alkoxy or phenylazo) aralkoxycarbonyl, haloaryloxycarbonyl, or haloalkylcarbamoyl.

2. A process according to claim 1 wherein R is alkanesulfonyl or arenesulfonyl, and X is halo(lower)alkoxycarbonyl, ar(lower)alkoxycarbonyl, 4-nitrobenzyloxycarbonyl, 4-methoxybenzyloxycarbonyl, 3,4-dimethoxybenzyloxycarbonyl, or 4-hydroxy-3,5-di(tert)butylbenzyloxycarbonyl.

3. A process according to claim 2, wherein R is arenesulfonyl.

4. A process according to claim 3, wherein R is tosyl and X is thrihalo(lower)alkoxycarbonyl, phenyl(lower)alkoxycarbonyl, 4-nitrobenzyloxycarbonyl, 4-methoxybenzyloxycarbonyl, 3,4-dimethoxybenzyloxycarbonyl, or 4-hydroxy-3,5-di(tert)butylbenzyloxycarbonyl.

5. A process according to claim 4, wherein X is 2,2,2-trichloroethoxycarbonyl or 4-nitrobenzyloxycarbonyl.

6. A process according to claim 5, wherein the substituent at the 7th position is acylamino as defined in claim 1.

7. A process according to claim 6, wherein the substituent at the 7th position is phenylacetamido.

8. A process according to claim 5, wherein X is 4-nitrobenzyloxycarbonyl and the substituent at the 7th position is amino.

9. A process according to any one of claims 2–8 or 1 wherein the reducing agent is zinc in admixture with formic acid.

10. A process according to claim 1 wherein zinc powder is added to 2,2,2-trichloroethyl 7-(2-phenylacetamido)-3-tosyloxy-3-cephem-4-carboxylate dissolved in formic acid with ice cooling and the product compound (II) is 7-(2-phenylacetamido)-3-cephem-4-carboxylic acid.

11. A process according to claim 1, wherein zinc powder is added to 4-nitropbenzyl 7-(2-phenylacetamido)-3-tosyloxy-3-cephem-4-carboxylate dissolved in 90% formic acid under ice cooling and the product compound (II) is 7-(2-phenylacetamido)-3-cephem-4-carboxylic acid.

* * * * *